United States Patent [19]

Valetas

[11] 4,206,222

[45] Jun. 3, 1980

[54] METHOD FOR PREPARING A SUBSTANCE HAVING PROPERTIES AGAINST COLLAGEN DISEASES AND PRODUCTS OBTAINED

[75] Inventor: Jean Valetas, Tulle, France

[73] Assignee: Société Civile Particuliére de Brevets Suffren, Paris, France

[21] Appl. No.: 931,982

[22] Filed: Aug. 8, 1978

Related U.S. Application Data

[63] Continuation-in-part of Ser. No. 829,006, Aug. 30, 1977, abandoned.

[30] Foreign Application Priority Data

Jun. 23, 1977 [FR] France .................. 77 19224

[51] Int. Cl.$^2$ .................. A61K 31/365; A61K 35/78; C07D 309/30
[52] U.S. Cl. .................. 424/279; 260/343.5; 424/195
[58] Field of Search .................. 260/343.5; 424/279, 424/195

[56] References Cited

U.S. PATENT DOCUMENTS

| 3,584,123 | 6/1971 | Tubery | 424/195 |
| 3,839,553 | 10/1974 | Martinez et al. | 424/74 |

OTHER PUBLICATIONS

Virtanen, A., et al., *Acta Chem. Scand.* 8(6), 1091–1093 (1954).
Molodozhnikova, L., et al., *Sb. Nauch. Rab. Vses. Nauch. Issled. Inst. Lek. Rast.* 1970, No. 1, 164–168 [*Chemical Abstracts,* 76:70088c (1972)].

*Primary Examiner*—John D. Randolph
*Assistant Examiner*—Richard A. Schwartz
*Attorney, Agent, or Firm*—Holman & Stern

[57] ABSTRACT

This invention relates to the chemical and pharmaceutical industries.

An active agent is extracted from ferns with a water-alcohol mixture. The essential compound is a delta-lactone having 8 carbon atoms, obtained as a monomer and/or as polymers, and which may be under the form of a chelate salt. It is useful mainly as the active substance in drugs for the treatment of diseases accompanied by collagen alterations.

15 Claims, No Drawings

METHOD FOR PREPARING A SUBSTANCE HAVING PROPERTIES AGAINST COLLAGEN DISEASES AND PRODUCTS OBTAINED

This application is a continuation-in-part of application Ser. No. 829,006, filed Aug. 30, 1977, now abandoned.

The present invention relates to the production of active substances which are particularly useful in the pharmaceutical field as well as to these substances and their different applications.

According to the present invention it was discovered that it is possible, by submitting ferns to an extraction process with water-alcohol mixtures, to obtain a substance that is deprived of the toxicity of the starting ferns and which shows a surprising activity against diseases connected with alteration of collagen metabolism. Analytical tests carried on such a substance have lead to believe that it would have a structure of a δ-lactone having 8 carbon atoms. However the invention also extends to similar compounds which might differ from the specific formula which has been determined by the only analytical means presently available. Furthermore, the invention is not restricted to a specific extraction method or to the pharmaceutical uses. It also extends to the chemical substances per se and to their uses out of the pharmaceutical field, especially as intermediate compounds for the preparation of chemical derivatives and in the dye industry.

Considering the chemical formula, although as a non limiting feature of the invention, a substance according to the invention essentially contains a $C_8$ delta-lactone comprising an ene-diol grouping in tautomeric equilibrium with the corresponding keto form, and more specifically the levorotatory optical isomer showing the following formula:

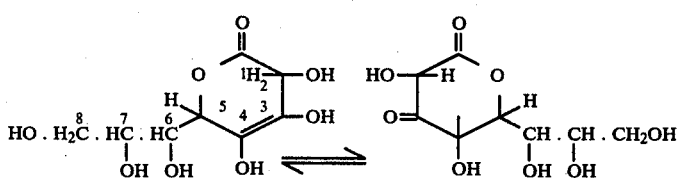

(α)-D-gluco-octono-δ-lactone-ene-diol and the corresponding keto compound), which lactone compound may be as a monomer or a polymer and optionally in salt form, preferably as a salt formed with a pharmaceutically acceptable base.

The acidic lactone monomer crystallizes from methanol in the form of rosettes or plates having a melting point around 160° C. (decomposition). It is most often obtained as a mixture with polymers, and above all with a polymer with the general formula $(C_8H_{12}O_8)_{57}$, with a molecular weight of 13500 and containing about 39.41% C and 5.96% H. These polymers may be in the form of salts like the monomer.

The calcium salts are advantageous for most industrial and therapeutical uses because they are stable, non toxic, non hygroscopic, and water-soluble. A preferred substance according to the invention is therefore the calcium salt of the optical monomer isomer having the following formula:

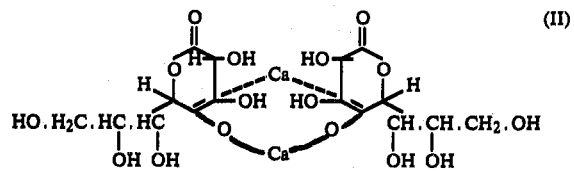

which is a derivative of the levorotatory lactonic form of the monomer D-gluco-octono-delta-lactone-3,4-enediol.

Substances according to the invention, which may be used as active agents in medicaments, also comprise those which are essentially constituted by at least one $C_8$ deltalactone compound such as may be extracted from ferns by water-alcohol extraction, or a derivative thereof formed with a pharmaceutically acceptable base. The object of the invention also includes a process for obtaining such substances which comprises the steps of extracting dried ferns with a mixture of ethanol and water, eliminating from such extracts at least the tannins, chlorophyll and other pigments, and subsequently alcohol, then preferably also at least the sugars and sulphates. In a preferred embodiment of the process of the invention, the tannins, chlorophyll and other pigments are eliminated by treating the alcoholic extract with active charcoal, the alcohol is eliminated by distillation, the cations are eliminated using ionic exchange resins, whereas the sulphates are eliminated after neutralization with calcium hydroxide of the water solution containing the mixture of the calcium salts of the monomer and its polymers.

An essential step of the method of the invention is the water-alcohol extraction which is advantageously carried out on ground dried ferns down to a water content of less than 10% by weight and preferably equal to about 5% by weight, using a mixture of water and ethanol which contains at least 20%, and preferably from 40 to 95% by volume of ethanol. In this mixture however, ethanol may be replaced by another alcohol which should be miscible with water, such as methanol or propanol. The amount of the water-alcohol mixture is generally from 3 to 20 liters per kilogram of the fern powder (grain size between 200 and 400 mesh) and the extraction is preferably operated at boiling temperature during from 0.5 to 10 hours. The previous drying step may be advantageously performed at a temperature from 45° C. to 80° C. during 14 to 20 hours.

The subsequent purifying step is preferably performed by contacting the extract with activated charcoal (used for instance in an amount of from 150 g to 400 g per kilogram of fern powder), but it can also be performed using any other known absorbent of tannins. In a preferred embodiment, the method of the invention then further comprises the steps of concentrating the extract by evaporating the alcohol at a temperature from 25° C. to 75° C., further purifying the extract by contacting it with a cation exchange resin in the hydrogen ionic form, then neutralizing the extract to a pH preferably from 3 to 7, particularly from 4.5 to 6.5, and removing the precipitated insoluble materials. The extract from which the cations have been removed by ions exchange, has advantageously a pH from 0.9 to 1.2.

In order to further purify the substance obtained, the aqueous extract may be concentrated by evaporating water under a vacuum such that the temperature does not exceed a value from 25° to 75° C. The concentrated extract may then be admixed with methanol or with a mixture of methanol and ethanol preferably containing from 30 to 70% of each of these components by volume. The precipitate formed is recovered and dried. It constitutes a substance according to the invention, essentially under the form of a calcium salt.

According to another embodiment of the invention, a purification step may be performed starting from an aqueous solution of the calcium salt, submitting it to a chromatography process so as to separate a monomer calcium salt the molecular weight of which is between 500 and 600. The calcium ions may be removed from this salt by ion exchange on a strong cationic resin under the hydrogen form. The solution may then be concentrated by evaporation. It contains the acid monomer lactone which can be crystallized from anhydrous methanol.

Generally, the molecular weight of the substance of the invention varies roughly from 200 to 20000 because of the presence of polymers. When it is desired to obtain a substance with a high concentration of monomer, for instance for pharmaceutical uses, the extraction is preferably performed with a water-ethanol mixture containing not more than approximately 25% water. If instead, one wishes to obtain an extract with a high concentration of polymers, it is advantageous to perform the initial extraction with a water-ethanol mixture containing more than 25% water although less than 80%. The polymers may also be obtained by repeated lyophilization (freeze-drying) from aqueous solutions of the monomer or by the addition of chloroform and/or secondary butanol to a solution of the monomer in methanol.

As the starting material in the method of the invention, any fern may be used, especially those from the group comprising the species of the genera Davallia, Dryopteris, Oleandra, Phyllitis, Polypodium and Pteridium, and preferably the species of the Polypodium and Pteridium genera. Such species of ferns are listed in Index Londinensis (Oxford).

The substance of the invention may be extracted from any part of the mentioned ferns, but it is more practical to harvest only the aerial parts (parts above the ground) of adult plants.

The substances obtained according to the invention, whether as a monomer or as polymers and whether as an acidic lactono-ketone or as chelate salts, may be used in various industries. In particular, it is possible to prepare dyes by reacting them with a chromogen reactant, and more specifically by letting the monomer react with methylbenzyl-thiazolidone-hydrazine in the absence of ferric ions.

However, the most valuable uses of the substances of the invention result from their pharmaceutical activity against disorders of the collagen metabolisms. They can be used as the active agent in drugs which may contain them for instance in an amount of 5 mg to 100 mg per unit dose, in a pharmaceutically acceptable vehicle of any known type. In such uses, the substances used are preferably monomers and preferably monomer salts such as the calcium salt. The calcium salt is advantageous due to its stability but other salts may also be used such as the sodium salt or the potassium salt which can be prepared by reacting the acidic lactono-ketone with corresponding bases.

The drugs may be administrated orally to humans, for instance at daily doses from 10 mg to 500 mg in the treatment of diseases in which collagen alterations are involved, such as psoriasis. It follows from the foregoing that beneficial effects may be envisioned also in the treatment of arthrosis and arthritis, of varicose ulcers, stomach ulcers, lupus erythematosus and to stimulate wound healing particularly in the case of surgical wounds.

The active substances of the invention are practically devoid of toxicity, despite the fact that ferns are often toxic in animals, mainly in cattle, horses and sheep; following chronic ingestion of ferns these animals exhibit a variety of toxic symptoms, known under the denomination of bracken-fern poisoning.

Practical examples given below have been selected to provide a better understanding of the invention, but should by no means be considered limiting. All proportions are indicated by weight except when otherwise stated.

EXAMPLE I

Aerial parts of adult ferns of the species Polypodium aureum are harvested, dried rapidly in order to avoid fermentation at a temperature not exceeding 70° C. and ground to obtain a powder with about 5% moisture. 1.5 kg of this powder is extracted with a mixture of about 12 liters of ethanol 95° and 4.5 liters of water (distilled) for one hour under reflux; the extract is then filtered or drained.

The water-alcoholic extract is clarified with activated charcoal in powder form and filtered.

The alcohol in the filtrate is evaporated under reduced pressure and the aqueous residue is passed through a conventional strong cationic exchange resin.

The eluate is neutralized with calcium hydroxide powder up to a pH of 5 approximately. After filtration, the filtrate is concentrated by evaporation under reduced pressure to about 0.2 liter.

A precipitate is produced by addition of about 0.6 liter of methanol; it is filtered and washed subsequently with pure methanol.

The precipitate is dried at a temperature not exceeding 35° C. and ground to obtain about 20 g of white powder.

This salt is purified by dissolution in about 100 ml of water followed by treatment with activated charcoal; it is then filtered and dried by freeze-drying. The lyophilized material is ground to obtain a substance practically devoid of impurities which after various analytical methods appears to be formed to the extent of approximately 90% by the calcium salt of a lactone monomer with the proposed formula:

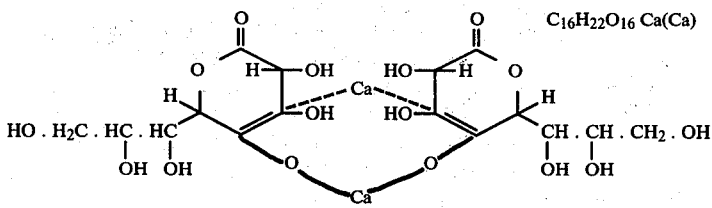

and to the extent of about 10% by calcium salts of homopolymers of said monomer.

This substance is a white powder, homogenous, with a bitter and salty taste, that dissolves completely in water in practically all proportions and is insoluble in alcohol. The water solution is slightly yellow. A 2% (w/w) solution has a pH of around 6.25 and a specific rotation at 25° C. $(\alpha)_D^{25} = -7.10$.

The powder has a calcium content of 15.95% approximately.

By reacting it with methyl-benzyl-thiazolidonehydrazine, in the absence of ferric ions, cyanine dyes are obtained which are green, blue, red and purple and may be separated by chromatography. These dyes respond to the general empirical formula of: $C_{24}H_{25}N_6S_2O_7$.

EXAMPLE II

The purified salt substance of example I is dissolved in water in an amount sufficient to obtain a concentration of about 10%. The aqueous solution is passed through a conventional polysaccharide-dextran chromatography column (Sephadex) to separate a monomer fraction having a molecular weight from 500 to 600 from a polymer fraction having a higher molecular weight. The monomer fraction is treated with a conventional strong cation exchange resin in hydrogen form, then by a conventional weak anion-exchange resin. The solution thus deionized is concentrated under reduced pressure at a temperature not exceeding 50° C. until a semisolid, transparent residue is obtained which is dissolved in anhydrous methanol. The methanol solution is concentrated under reduced pressure at a temperature below 40° C. until it turns opalescent and then it is left until the desired product crystallizes in plates (rosettes).

This substance has a pronounced but not unpleasant acid taste. It is stable in the air at ambient temperature. Its melting point is 160° C. with decomposition. It is soluble in methanol (1 g/20 ml) and in ethanol (1 g/50 ml) and insoluble in lipophilic solvents.

Elementary analysis by known methods gives around 40.18% C and around 5.08% H, but no nitrogen, sulphur or other elements except oxygen. The proportion of carbon and hydrogen is 2 C to 3 H. The molecular weight evaluated by saccharide-dextran column chromatography falls between 200 and 250.

The empirical formula $C_8H_{12}O_8 = 236$ corresponds to the theoretical values: 40.67% C and 5.12% H and the product obtained by the process described above corresponds, with slight analytical variations, to the mentioned values.

The infra-red spectrum in tetrahydrofurane shows an intense peak at 1732 cm$^{-1}$, characteristic of a delta-lactone, peaks between 1640-1655 cm$^{-1}$ characteristic of a double-bond and at 3000 cm$^{-1}$ characteristic of enolic groups.

Trimethyl-silyl derivatives prepared according to the technique described by De Jongh et al in the Journal of American Chemical Society (JACS) 91 1728 (1969) reveal, upon analysis, an analogy in configuration with an aldohexose, like D-glucose or D-galactose, because of the arrangements of the -H and -OH's on the asymmetric carbons.

The N.M.R. spectrum of the lactone in DMSO-D$_6$ shows the 12 protons: (ppm) 6.52=3 H; 4.35-4.46=1 H; 3.65-3.60=5 H; 3.43-3.19=2×½ H, and 2.50 to 2.80=2 H.

The aforementioned analytical results suggest for the substance the following structural formula of a lactone: D-gluco-octono-delta-lactone-3,4-ène-diol, in equilibrium with the corresponding ketotautomer:

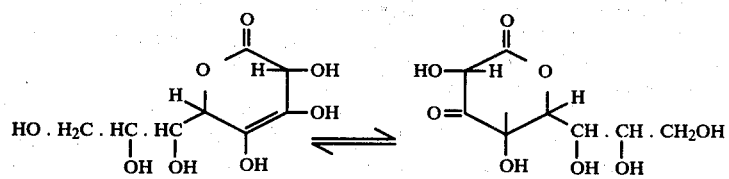

This compound gives readily metallic salts, particularly sodium, potassium, magnesium and calcium salts by reaction of the acidic lactone with corresponding bases (hydroxides).

The uncrystallized lactone is hygroscopic and unstable; if left on the bench it assumes a syrupy aspect. Its aqueous solution (10 g/liter) has a pH of approximately 3.

The specific rotation of the lactone at 25° C. is $(\alpha)_D^{25} = -6.7$ (1.6% in water), that of its sodium salt is approximately $-11.6$ (2.5% solution in water).

The ultraviolet absorption spectrum of the lactone shows a maximum at 280 nm ($E_{1cm}^{1\%} = 14.42$) whereas its sodium salt shows a shift of this maximum to a shoulder between 240 and 270 nm.

The reaction of the lactone with methyl-benzyl-thiazolidone-hydrazine (in the absence of ferric ions) gives rise to a characteristic purple tetraazo-pentamethine-cyanine having a mass spectrum, mass-chromatography and elementary analysis corresponding to a C$_8$ lactone.

EXAMPLE III

The procedure of example I is followed except that ferns of the Polypodium Percussum Cav. species are used and the extraction is performed with a mixture of about 5 liters of ethanol 95° and about 12 liters of water.

A whitish solid is thus obtained, that is soluble in water and consists mostly of the calcium salt of various polymers, mostly of polymer $(C_8H_{12}O_8)_{57}$, (MW=13500).

Analysis: C=39.41; H=5.96%.
Specific rotation at 25° C.=+99.9.

By a process similar to that of example II, a similar acid lactone monomer can be obtained which has a MW from 200 to 250 and similar properties.

EXAMPLE IV

Fresh aerial parts of the fern Pteridium caudatum Max., are dried in an oven with forced hot air draft at 60° C. during 18 hours and then ground to a particle size between 200 and 400 mesh.

One kilogram of the ground dried powder obtained is extracted in a continuous manner with 10 liters of 75% ethanol, and the slurry is filtered off.

The filtered extract is stirred with 250 g activated charcoal (vegetable or animal origin, for instance activated charcoal, Merck, Darmstadt, West Germany) for one hour, whereby the chlorophyll, the carotenoid pigments, tannins, coumarins, pterosins and other impurities are removed. The mentioned stirring is performed at room temperature preferably and the slurry is filtered off.

The filtered extract is evaporated under a moderate vacuum (50 to 150 mm Hg) at 50° C. until the alcohol is removed.

The aqueous residue (about 2.5 liters) is subjected to a cation exchange by a column of one kg of known strong cation exchanger in the hydrogen ionic form (for instance strong-cation exchange resin No. I, Merck, Darmstadt, West Germany), whereby all cations of the said residue are exchanged for hydrogen ions and the resulting solution reaches a pH of about 1.0.

The said acid aqueous residue is then neutralized with solid calcium hydroxide under stirring to pH 6 (about 10 g of solid calcium hydroxide is needed), whereby organic acids such as malic, fumaric, succinic, etc., and the sulphates precipitate and are filtered off.

An evaporation is then effected under a moderate vacuum (50 to 150 mm Hg) at 50° C., whereby a syrupy residue is obtained. This syrupy residue is shaken with one liter of a 1:1 mixture of ethanol and methanol for 30 minutes to 2 hours, preferably for one hour, whereby the calcium salt precipitate is formed and is filtered off, (for instance, in a press-filter on paper or cellulose discs) or centrifugated. The said precipitate is stirred with about one liter of methanol at 50° C. for one hour and then filtered off, whereby the last traces of sugars are removed.

The said calcium salt precipitate is then dried at 50° C., dissolved in water to a concentration of 30% and is then lyophilized. More generally, the concentration of the aqueous solution may vary from 5% to 50%.

Yield: 8–10 of alpha-D-gluco-octono-delta-lactono-ketone calcium salt chelate. (Ca: 15–16%).

EXAMPLE V

The calcium salt obtained in example IV is dissolved in water to obtain a 20% aqueous solution which is then passed through a strong-cation exchanger resin in its hydrogen ionic form, so as to remove calcium ions. The solution is then concentrated by evaporating the water under a limited vacuum at a temperature never to exceed 50° C., then dissolved in methanol to give a 50% solution. The acidic lactone (delta-lactone-ketone) crystallizes as a white powder slowly in the cold (4° C.). It is filtered off and dried in vacuo under potassium hydroxide, melting point 160° C. (decomposition), $(\alpha)_D^{25} = -7.2$ (2.5 in water).

Found: C=40.18; H=5.08; O=53.84%. Calculated for $C_8H_{12}O_8$: C=40.67; H=5.12; O=54.21%.

3-methyl-2-benzothiazolone hydrazone derivative: (purple dye)

Found: C=47.35; H=4.35; N=13.84; S=10.88; O=18.32%. Calculated for $C_{24}H_{25}N_6S_2O_7$: C=50.24; H=4.39; N=14.65; S=11.16; O=19.54%.

By chromatography on unidimensional thin layer cellulose and by making use of a solvent consisting of formic acid, methyl-ethylketone, tertiary butyl alcohol, water (15:25:35:25), there is detected a spot with a mean RF coefficient of 0.7 by the use of aniline-ribose according to the method described by Higgins and von Brand, Anal. Biochem., Vol. 15, p. 122 (1966) and by use of 3-methyl-2-benzothiazolone hydrazone described by Sawicki, E. et al, Anal. Chem., Vol. 33, p. 93 (1961). The said hydrazone test takes advantage of the fact that the said delta-lactono-ketones give cyanine dyes with said reagent directly, (ref. Hünig. S et al, Angew. Chemie internat. Ed., Vol. 1, p. 640 (1962).

Fluoro-silylation of a dimethylsulphoxide solution of the alpha-D-gluco-delta-lactono-ketone with N,O-bis (trimethylsilyl)-trifluoro-acetamid gives a single maximum in vapour phase chromatography, with a retention time of 210 seconds. To the contrary, silylation with hexamethyldisilazan and trimethyl-chlorosilan of said solution shows only the maximum and the mass of alpha-D-glucose in the mass chromatogram.

The mass of 236 for the alpha-D-gluco-octono-delta-lactono-ketone is conveniently determined by permethylation in a solution of dimethyl sulphoxide of said compound with methyl iodide and sodium hydride, by combining vapour phase chromatography, mass spectrum and a computer.

The delta-lactone ring of alpha-D-gluco-octono-delta-lactone-ketone is conveniently revealed in the infrared spectrum of its solution in tetrahydrofurane, with a maximum of 1732 cm$^{-1}$.

The position of the keto group of alpha-D-gluco-octono-delta-lactono-ketone at carbon-3 is conveniently determined through its dinitrophenylhydrazone=CH-CH(OH)-COOH($C_9H_{10}N_4O_6$) prepared according to Roe and Kuether (J. biol. Chem., 147 399 (1943).

Calculated: C=39.99; H=3.73; N=20.73% Found: C=38.70; H=3.16; N=20.16%

EXAMPLE VI

The free delta-lactono-ketone obtained in example V by removing the calcium from an aqueous solution of a calcium salt chelate with a strong-cation exchange resin is neutralized with 0.1 normal to 2 normal, preferably 1.0 normal solution of sodium hydroxide or potassium hydroxide up to pH 4.5 to pH 6.5, preferably to pH 5, and the solution is lyophilized.

EXAMPLE VII

The ethanol described in example V is substituted by another alcohol miscible with water, for instance methanol, n-propanol or 2-propanol. The said alcohols are used as such or mixed with water from 25% to 95%.

EXAMPLE VIII

The same procedure as in example IV is used for treating the following fern species:

*Davallia divaricata* Bl., Index Londinensis, Oxford, 1921, vol. 2, p. 437, described previously by C. L. Blume in Enumeratio Leyden, 1828.

*Dryopteris crassirhizoma* Nakai, Index Londinensis, Suppl. 1 page 339 described by Makino in the Illustrated Flora of Japan, 1924, page 1243.

*Oleandra neriiformis* Cav. described by A. J. Cavanilles in the Anales de Historia natural, 1799, vol. 1, page 108 and also described with the denomination of *Oleandra pistillaris* Sw. by O. Swartz, Index filicum, Genera and Species Filicum, 1801.

*Phyllitis scolopendrium* Newman, Index Londinensis, Oxford, 1921, vol. 5, page 79, described previously by E. Newman in Waller's New Brit. Domestic Herbarium, vol. 17, 1882.

*Polypodium aureum* Linné, Index Londinensis, Oxford, 1921, vol. 5, page 214, described previously under the synonyms *Phlebodium aureum* Smith in Index Filicum Christensen, H. Hagerup, Hafniae 1906, page 511 and as *Polypodium leucatomos* poir. in Poiret, Enc. Meth. Bot., 1804, vol. 5, page 508.

*Polypodium crassifolium* Linné, described by Linné in Species plantarum, Stockholm, 1753–63, page 1083, also described as *Dipteris crassifolia* by J. Smith in the Journal of Botany 1842, vol. 1, page 196, and as *Polypodium enocarpum* Kunze in the G. Syn. Plant. Linné, Berlin 1834.

*Polypodium decumanum* Willdenow, described in Mettenius, Abh. Senckeng. Nat. Ges., vol. 2, tome 2, 1856–58 and in Ann. Bot. 1917, vol. 31, tome 1, with FIGS. 6 and 7, also described by V. Vareschi in Flora de Venezuela, Helechos, Caracas, 1968, vol. 1, tome 2, page 945; under the denomination *Phlebodium multiseriale* T. Moore in Index Londinensis, Oxford, 1921 and in T. Moore and Houlston Gard. chron. London, 1855, page 469 and as *Chrysopteris dictyocallis* Féé in Féé A.L.A.: Memorandum about fern families, Paris 1844–66 and Strasbourg 1850–52 and 1853.

*Polypodium lanceolatum* Linné, Index Londinensis, Oxford, 1921, vol. 5, page 217, described previously by Lamack in 1797 in Ill. vt. 866, FIG. 1 and in Berichte der botanischen Gesellschaft, 1913, vol. 31, page 486.

*Polypodium percussum* Cav., Index Londinensis, Oxford, 1921, vol. 5, page 220, described previously by A. J. Cavanilles in "Description de plantas que Cavanilles demostró", Madrid 1802.

*Polypodium triseriale* Swartz described in Index Filicum, Copenhagen, 1906, Hagerup, and in O. Swartz, Nova genera and species plantarum, Stockholm, 1788.

*Pteris aquilina* Linné, Index Londinensis, Oxford, 1921, vol. 5, page 310, previously described as *Pteridium aquilinum* Kuhn in Max Kuhn and Thomé Flora Deutschl., vol. 6, 1886, including in particular the variety *latiusculum* Underwood of the mentioned species.

EXAMPLE IX

The syrup containing the calcium-salt-chelate of the alpha-D-gluco-octono-delta-lactono-ketone and sugars obtained in example V is devoid of toxicity, whereby it constitutes a pharmaceutical preparation. The said syrup is conveniently lyophilized and contains about 20% of the said delta-lactono-ketone in its calcium-salt-chelate form.

EXAMPLE X

Upon addition in vitro of 1 to 2 micrograms of the sodium or of the potassium salt of the alpha-D-gluco-octono-delta-lactono-ketone of example VII or of the free delta-lactono-ketone of example VI, to the aqueous, saline or acid extracts of the skin of psoriatic and arthritic patients, their rotatory power reaches normal values within 30 minutes.

It should be noted that psoriasis is already known as a disease connected with disorders of the collagen metabolism (Namey and Rosenthall, Arthritis and Rheumatism, vol. 19, No. 3, 1976).

EXAMPLE XI

Toxicity Evaluation

The purified, lyophilized and ground calcium salt of example I is used.

In the first series of tests designed to determine the acute toxicity of the product, a single dose of 250 mg/kg is administered orally to 10 albino rats of the Wistar strain. This massive dose does not produce any mortality or noticeable alteration in the behaviour of the animals.

In a second series of tests, a single dose of 1000 mg/kg is administered orally to a group of 20 mice of Swiss Albino-OFI strain weighing an average of 20 grams. This massive dose does not induce any alteration in the behaviour of the mice during the ensuing 14 days. The autopsy performed on the 15th day does not reveal any macroscopic lesion of the major organs.

Thus the lethal dose ($DL_0$) by the oral route is higher than 250 mg/kg in the rat and higher than 1000 mg/kg in mice.

In a third series of tests, designed to determine sub-chronic toxicity in the rat, four groups, of 12 animals each are used (Wistar strain) 6 males and 6 females, with an initial body weight of approximately 120 g. Each day, for four consecutive weeks the following doses are administered by stomach tube: 5 mg/kg to the rats of the first group, 10 mg/kg to the rats of the second group, 20 mg/kg to the rats of the third group, the fourth group serving as controls and receiving distilled water in the same volume.

No alteration in behaviour is noted either during the treatment period or for the two weeks following the termination of treatment.

The growth curve for males and females shows no difference between groups, including the control group.

Routine hematology shows uniform results in all lots including the control group.

After 28 days of treatment, half the animals are sacrificed (3 males and 3 females in each group) whereas the other half are kept for 14 days following the termination of treatment. No significant difference is observed, either macroscopically or histologically, between control and treated animals. No detectable lesion was therefore produced by the treatment.

It follows that under the experimental conditions described above the administered substance proved to be devoid of toxicity.

EXAMPLE XII

Effect On Collagen

Human skin samples (whole skin) of appr. 100 mg total weight are taken by biopsy from the forearm of 6 arthritic patients, 6 psoriatic patients and from 6 healthy control subjects. The subjects, males and females, range in age from 13 to 50 years.

Collagen is extracted in the conventional way from three pooled samples corresponding to the three separate groups: arthritic patients, psoriatic patients, and healthy subjects.

Each sample is homogenized separately and extracted consecutively with distilled water, then with 0.45 M NaCl solution and finally with 0.1 M acetic acid. Each time a quantity of liquid is used that corresponds to 20 times the weight of the wet samples. The homogenized samples are left standing at 2° C. overnight. The homogenates are then centrifuged and the supernatant is obtained by suction from below the floating lipid layer.

The optical rotatory power of each sample is measured at 578 nm and 27° C. A marked lowering of the rotatory power of the soluble collagen fractions is observed on samples from arthritic and psoriatic patients, as compared with healthy controls. The rotatory power of the patients is around $-200$ to $-600$ in the aqueous homogenate, while that of the controls is around $-2000$. Salt-soluble collagen fractions of the patients have a rotatory power around $-1000$ to $-5000$ whereas it is around $-12,000$ in healthy subjects. Acid-soluble collagen fractions of the patients present a rotatory power around $-12,000$ to $-24,000$, versus approximately $-40,000$ to $-60,000$ in healthy subjects.

Upon addition in vitro of 1 to 2 micrograms of the Calcium salt (purified, lyophilized and ground) of example I to the aqueous, saline or acid extracts of the skin of the patients, the rotatory power reaches normal values within 30 minutes.

EXAMPLE XIII

Clinical Evaluation

A trial is performed on 11 patients of 24 to 71 years of age, suffering from long-lasting resistant psoriasis. All have been treated previously, without durable success or stable improvement for at least one year with several conventional drugs, such as, corticoids and vitamin A for systemic therapy, tar preparations, or Caryolysine applied topically and psoralenes with U.V. irradiation as mixed treatment.

Psoriasis is a disease with collagen alterations characterized by spectacular skin lesions, that is found in the human species only and thus does not lend itself to experiments in animals.

In this trial, 3 to 4 capsules (according to body weight and/or severity) are administered daily by oral route without any other treatment, each capsule containing 12 mg of the calcium salt, purified, lyophilized and ground of example I, 10 mg of levilite, 20 mg of lactose and 10 mg of talcum powder. The dose of the calcium salt of example I administered to humans in this trial corresponds to about 500 times less than the dose found devoid of acute toxicity in the rat, 2000 times less than the dose found devoid of acute toxicity in mice and 40 times less than the dose found devoid of subchronic toxicity in the rat.

The observations on the treatment of these patients are shown in the attached chart.

| Sex & Age | Type of Psoriasis | ANAMNESIS | | TREATMENT Duration | RESULTS |
|---|---|---|---|---|---|
| | | Duration | Remissions- previous treatments | | |
| M 71 | Palmo- plantar Pu tulous Nails | 3 yrs | Incomplete remissions dermo-corti- coids | 3 mo | Complete regression; Remarkable improvement of general status |
| M 71 | Ps. vulg. 60% body surface +nails+ scalp | 15 yrs | Incomplete regression tar + dermo- corticoids | 3½ months | Complete regression |
| M 24 | Ps. vulg 40% body surface +nails+ scalp | 12 yrs | No regres- sion Dermo-corti- coids, Vit A orally | 6 mo | Evolution towards annular psoriasis Cons. improvement of scalp and peri- phery of scales |
| M 26 | PS. vulg. 15% body surface +nails | 1 yr | Incomplete with Goekerman + Carolysin topically | 5 mo | Regression 80% of lesions; annular scales knees & elbows |
| M 58 | Ps. univ. | 22 yrs | Incomplete regression Goekerman Roche-Posay | 3 mo | 70% regression on scalp, back, abdomen, buttocks |
| M 26 | Psoriatic onyxis+ scalp + thorax | 11 yrs | Incomplete regression Goekerman local corti- coids | 3 mo | Improvement of nails & thorax scales |
| M 42 | Ps. vulg. 40% body surface + scalp | 9 yrs | Incomplete regression Caryolysin | 6 weeks | Improvement scalp buttocks, left calf |
| M 43 | Ps. vulg. 50% body surface + scalp | 3 yrs | No regres- sion Dermo-corti- coids | 6 weeks | Clear improvement scalp, ears, hands + peeling on trunk & limbs |
| M 27 | Ps. vulg. +nails+ scalp | 3 yrs | No regres- sion Dermo-corti- | 1 month | Improvement hands Peeling trunk |

| Sex & Age | Type of Psoriasis | ANAMNESIS | | TREATMENT | RESULTS |
|---|---|---|---|---|---|
| | | Duration | Remissions-previous treatments | Dura tion | |
| M 55 | Ps. palmoplantar | 18 mo | coids No regression none (treatment) | 5 weeks | Clear improvement hands & feet |
| M 36 | Ps. vulg. + scalp + nails | 7 yrs | One remission Placentafil + Dermo-corticoids | 6 weeks twice w. intermitt. of 6 weeks | Clear improvement on scalp; larger scales on trunk |

In all cases, the clinical tolerance was perfect and confirmed by the biological tests carried out before, during and after treatment.

It is remarkable, that under this treatment the clearing of the lesions and the appearance of healthy skin, begins in the centre of lesion and extends towards the periphery.

It should be understood that the invention is by no means limited to the examples described herewith, and encompasses numerous variations known to the art, depending upon the uses considered.

It follows then that the novel compounds of this invention may be prepared by synthesis, following conventional procedures well known to chemists.

It may also be considered to obtain these novel compounds by extraction from plant species other than ferns, such as Lycopodiaceae and Equisetaceae.

I claim:

1. A method for preparing a substance having activity against collagen diseases, comprising submitting ferns to a water-alcoholic extraction effected using a water-alcohol mixture containing at least 20% of methanol, ethanol or propanol and purifying the extract by contacting it with activated charcoal or with a similar tannin absorbent.

2. A method according to claim 1, wherein aerial parts of ferns are previously dried and ground, then submitted to said extraction using a water-ethanol mixture containing at least 20% ethanol.

3. A method according to claim 2, wherein the ethanol content is from 40% to 95%.

4. A method according to any of claims 1 to 3 further comprising concentrating said extract by evaporating the alcohol therefrom at a temperature from 25° C. to 75° C., further purifying said extract by contacting it with a cation-exchange resin in hydrogen form, neutralizing the purified extract to a pH from 3 to 7, and removing the thus precipitated insoluble materials.

5. A method according to claim 4, wherein said extract is neutralized by adding thereto calcium hydroxide to a pH from 4.5 to 6.5 and the thus precipitated insoluble materials are removed.

6. A method according to claim 5 further comprising precipitating a lactone calcium salt from said extract by adding thereto methanol or a mixture of methanol and ethanol.

7. A method according to claim 6 further comprising lyophilizing said calcium salt.

8. A method according to claim 4, 5, 6, or 7, further comprising treating an aqueous solution of said lactone calcium salt by chromatography to separate a monomer fraction having a molecular weight from 500 to 600.

9. A method according to any of claims 6 to 8 further comprising contacting an aqueous solution of said lactone calcium salt with a cation-exchange resin in hydrogen form to obtain the corresponding acidic lactone.

10. A method according to claim 9 further comprising reacting said lactone with a pharmaceutically acceptable base.

11. A substance having activity against collagen diseases produced by the method according to any of claims 1 to 10.

12. A pharmaceutically active agent comprising at least one delta-lactone compound having 8 carbon atoms extractible from ferns by water-alcohol extraction, or a salt formed with pharmaceutically acceptable base.

13. A substance useful as an active agent against collagen alterations, constituted by a $C_8$ delta-lactone with the following formula

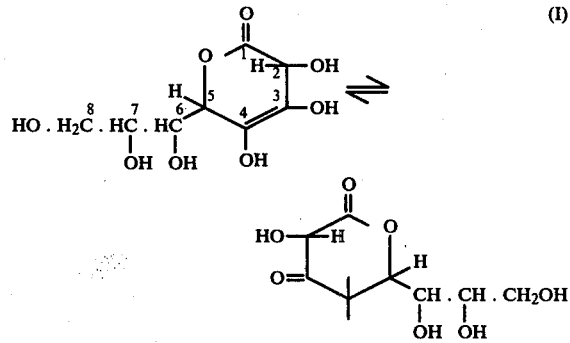

as a monomer or chelate salt thereof.

14. A substance according to claim 13, constituted by a calcium salt having formula

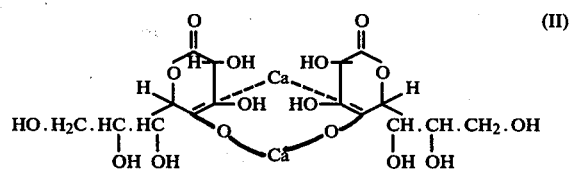

15. A medicament against collagen alterations comprising unit doses from 5 to 100 mg of an active agent according to claim 1 or a substance according to any of claims 11 or 14 and a pharmaceutical acceptable carrier.

* * * * *